United States Patent
Miki et al.

(10) Patent No.: US 7,368,608 B2
(45) Date of Patent: May 6, 2008

(54) 1-AMIDO-3-(2-HYDROXYPHENOXY)-2-PROPANOL DERIVATIVES AND A PROCESS FOR PREPARING 2-AMIDOMETHYL-1,4-BENZODIOXANE DERIVATIVES

(75) Inventors: Yasushi Miki, Osaka (JP); Masafumi Mikami, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 223 days.

(21) Appl. No.: 11/183,746

(22) Filed: Jul. 19, 2005

(65) Prior Publication Data

US 2006/0019993 A1    Jan. 26, 2006

(30) Foreign Application Priority Data

Jul. 20, 2004    (JP) .............................. 2004-211087

(51) Int. Cl.
C07C 217/02    (2006.01)
C07C 45/29    (2006.01)
C07D 209/48    (2006.01)
C07D 321/00    (2006.01)

(52) U.S. Cl. ...................... 564/349; 564/351; 568/306; 568/309; 549/200; 548/479

(58) Field of Classification Search ...................... None
See application file for complete search history.

(56) References Cited

U.S. PATENT DOCUMENTS

| 4,336,267 A | * | 6/1982 | Carlsson et al. ............. 514/538 |
| 4,463,190 A | * | 7/1984 | Lunsford et al. ........... 564/349 |
| 5,480,905 A |  | 1/1996 | Koda et al. |
| 5,935,973 A |  | 8/1999 | Birch et al. |
| 6,610,725 B1 | * | 8/2003 | Imbert et al. ................ 514/402 |

FOREIGN PATENT DOCUMENTS

EP    0 841 334    5/1998

OTHER PUBLICATIONS

V. Ferri et al., "Synthesis, Binding Affinities for α-Adrenoceptor and Eudismic Analysis of Chiral Benzodioxane Derivatives and Their Chiral Opened Analogues", Farmaco, Edizione Scientifica, Societa Chimica Italiana, Pavia, It, vol. 43, No. Suppl. 12, pp. 1153-1163, May 15, 1988, XP002063196, ISSN: 0430-0920.

Rainer Mohr et al., "H2-Antihistaminics. IXL. Base-substituted '(aryloxy)alkyl !guanidine derivatives and analogs with H2-antagonistic activity", Archiv Der Pharmazie (Weinheim, Germany), 321 (4), pp. 221-227, Coden: Arpmas; ISSN: 0365-6233, 1988, XP008056781.

Ellen W. Baxter et al., "Hindered Rotation Congeners of Mazapertine: High Affinity Ligands for the 5-HT$_{1A}$ Receptor", Bioorganic & Medicinal Chemistry Letters, 7(7), pp. 763-768, Coden: BMCLE8; ISSN: 0960-894X, 1997, XP004136126.

Alan M. Birch et al., "N-Substituted (2,3-Dihydro-1,4-benzodioxin-2-yl)methylamine Derivatives as D$_2$ Antagonists/5-HT$_{1A}$ Partial Agonists with Potential as Atypical Antipsychotic Agents", J. Med. Chem., 42, pp. 3342-3355, 1999.

* cited by examiner

Primary Examiner—Yvonne Eyler
Assistant Examiner—Yate' K Cutliff
(74) Attorney, Agent, or Firm—Wenderoth, Lind & Ponack, L.L.P.

(57) ABSTRACT

An 1-amido-3-(2-hydroxyphenoxy)-2-propanol derivative represented by the following formula (1),

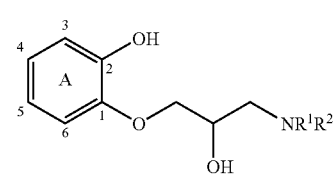

(1)

wherein cycle A may have further 1 to 4 substituents, and said substituent means a substituent selected from the group consisting of saturated or unsaturated C1-4 alkyl group, aralkyl group in which alkyl moiety has 1 to 4 carbon atoms, aryl group, halogen atom, halogenated C1-4 alkyl group, C2-5 alkanoyl group, mono or dialkylcarbamoyl group in which alkyl moiety has 1 to 4 carbon atoms, cyano group and nitro group, and the substituents at positions 3 and 6, or at positions 4 and 5 on the cycle A are different each other. Other ring may be fused at positions 3 and 4, or at positions 5 and 6 on the cycle A to form a condensed polycyclic hydrocarbon with the cycle A. $R^1$ is alkanoyl group or aroyl group, and $R^2$ is hydrogen atom, alkanoyl group or aroyl group, or $R^1$ and $R^2$ may be combined together with the N atom to form a cyclic imido group, which is useful as an intermediate of medicines, etc.

21 Claims, No Drawings

US 7,368,608 B2

1-AMIDO-3-(2-HYDROXYPHENOXY)-2-PROPANOL DERIVATIVES AND A PROCESS FOR PREPARING 2-AMIDOMETHYL-1,4-BENZODIOXANE DERIVATIVES

TECHNICAL FIELD OF THE INVENTION

The present invention relates to 1-amido-3-(2-hydroxyphenoxy)-2-propanol derivatives, optically active compounds thereof, a process for preparing them and a process for preparing 2-amidomethy-1,4-benzodioxane derivatives and optically active compounds thereof. These compounds are useful as an intermediate of medicines or physiological active compounds.

BACKGROUND OF THE INVENTION

2-Aminomethyl-1,4-benzodioxane derivatives, especially optically active compounds thereof are expected as a useful intermediate of preparing various medicines such as therapeutic agents for diseases of central nervous system (e.g., depression, anxiety, schizophrenia).

In general in regard to optically active medicines or intermediates thereof are required highly chemical purity and highly optical purity thereof. Therefore, it is an important problem to prepare optically active 2-aminomethyl-1,4-benzodioxane derivatives with highly chemical purity and highly optical purity.

Among the processes for preparing an 2-aminomethyl-1,4-benzodioxane derivative which have been developed, processes comparatively related to the process of the present invention are as follows:

(1) After 5-halo-2-hydroxybenzaldehyde and glycidyl tosylate are reacted in a base, 7-halo-2-hydroxymethyl-1,4-benzodioxane is obtained by oxidizing the formyl group of the reacted compound and then after tosylating it, an 2-aminomethyl-1,4-benzodioxane derivative is obtained by nucleophilic substitution with an amine derivative (WO 97/003071, Alan M. BIRCH, et al., J. Med. Chem., Vol. 42, No. 17, page 3342-3355 (1999)) and (2) By three-steps reaction starting from 2-benzyloxyphenol and epichlorohydrin or glycidyl tosylate in sodium hydroxide, 2-hydroxymethyl-1,4-benzodioxane is obtained and then further by chlorination, by nucleophilic substitution reaction of phthalimide and by degradation of the imido portion, an 2-aminomethyl-1,4-benzodioxane derivative is obtained (Japanese patent publication A 6-9613).

In case of the above method (1), as the formyl group is oxidative-degraded, an expensive oxidation agent (m-chloroperbenzoic acid) must be much used and its reaction is dangerous. On the other hand, in case of the above method (2), the yield is low and not satisfactory. Therefore, these methods (1) and (2) have problems as a preparation of it for industrial scale.

DETAILED DESCRIPTION OF THE INVENTION

The present inventors have extensively studied for dissolving the above problems, and as a result, they found an 1-amido-3-(2-hydroxyphenoxy)-2-propanol derivative and that by using this new compound as a starting compound, 2-amidomethyl-1,4-benzodioxane derivatives, especially their optically active compounds were easily obtained under the mild conditions, in highly chemical purity and highly optical purity. Thus the present invention was completed.

The present invention relates to an 1-amido-3-(2-hydroxyphenoxy)-2-propanol derivative represented by the following formula (1),

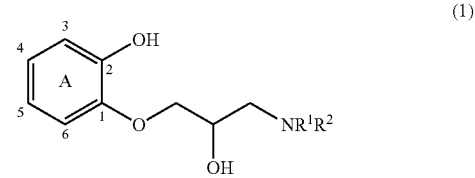

(1)

wherein cycle A may further have 1 to 4 substituents, and said substituent means a substituent selected from the group consisting of saturated or unsaturated C1-4 alkyl group, aralkyl group in which the alkyl moiety has 1 to 4 carbon atoms, aryl group, halogen atom, halogenated C1-4 alkyl group, C2-5 alkanoyl group, mono or dialkylcarbamoyl group in which the alkyl moiety has 1 to 4 carbon atoms, cyano group and nitro group, and the substituents at positions 3 and 6, or at positions 4 and 5 on the cycle A are different each other. Other ring may be fused at positions 3 and 4, or at positions 5 and 6 on the cycle A to form a condensed polycyclic hydrocarbon with the cycle A. $R^1$ is alkanoyl group or aroyl group, and $R^2$ is hydrogen atom, alkanoyl group or aroyl group, or $R^1$ and $R^2$ may be combined together with the N atom to form a cyclic imido group.

The present invention also relates to a process for preparing an 1-amido-3-(2-hydroxyphenoxy)-2-propanol derivative represented by the above formula (1), which comprises reacting an 2-alkoxyphenol represented by the following formula (2),

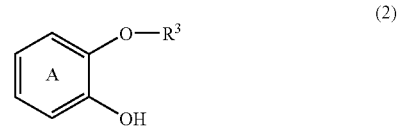

(2)

wherein cycle A is the same as defined above, $R^3$ is saturated or unsaturated C1-4 alkyl group, or aralkyl group in which the alkyl moiety has 1 to 4 carbon atoms, with a glycidylamide represented by the following formula (3),

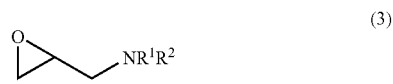

(3)

wherein $R^1$ and $R^2$ are the same as defined above, in the presence of fluoride salt, alkali metal carbonate or alkali metal hydrogencarbonate, and then eliminating the substituent $R^3$ to prepare the compound (1).

The present invention also relates to a process for preparing a 1-amido-3-(2-hydroxyphenoxy)-2-propanol derivative represented by the above formula (1), which comprises reacting an 2-alkoxyphenyl glycidyl ether represented by the following formula (4),

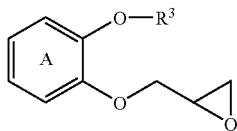

wherein cycle A and $R^3$ are the same as defined above, and an amide derivative represented by the following formula (5), $$R^1R^2NM \qquad (5)$$

wherein M is hydrogen atom or alkali metal and $R^1$ and $R^2$ are the same as defined above, in the presence of alkali metal carbonate, alkali metal hydrogencarbonate or quaternary ammonium salt, and then eliminating the substituent $R^3$ to prepare the compound (1).

The present invention also relates to a process for preparing an 2-amidomethyl-1,4-benzodioxane derivative represented by the following formula,

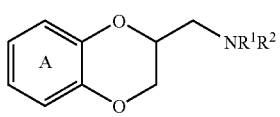

wherein cycle A, $R^1$ and $R^2$ are the same as defined above, which comprises converting the aromatic hydroxy group and the secondary hydroxy group of an 1-amido-3-(2-hydroxyphenoxy)-2-propanol derivative represented by the above formula (1), to acyloxy group and leaving group, respectively, and then subjecting it to intramolecular cyclization reaction to prepare the compound (6).

Furthermore, the present invention relates to a process for preparing an 2-amidomethyl-1,4-benzodioxane derivative represented by the above formula (6), which comprises reacting an 2-alkoxyphenol represented by the above formula (2), and a glycidylamide represented by the above formula (3), in the presence of fluoride salt, alkali metal carbonate or alkali metal hydrogencarbonate, and then eliminating the substituent $R^3$ to prepare an 1-amido-3-(2-hydroxyphenoxy)-2-propanol derivative represented by the above formula (1), or reacting an 2-alkoxyphenyl glycidyl ether represented by the above formula (4), and an amide derivative represented by the above formula (5), in the presence of alkali metal carbonate, alkali metal hydrogencarbonate or quaternary ammonium salt, and then eliminating the substituent $R^3$ to prepare the compound (1), and then, converting the aromatic hydroxy group and the secondary hydroxy group of the compound (1) to acyloxy group and leaving group, respectively and further subjecting it to intramolecular cyclization reaction to prepare the compound (6).

Scope of applicability of the present invention will become apparent from the detailed description given hereinafter. However, it should be understood that the detailed description and specific examples, while indicating preferred embodiments of the invention, are given by way of illustration only, since various changes and modifications within the spirits and scope of the invention will become apparent to those skilled in the art from this detailed description.

The process related to the present invention is schematically illustrated as follows:

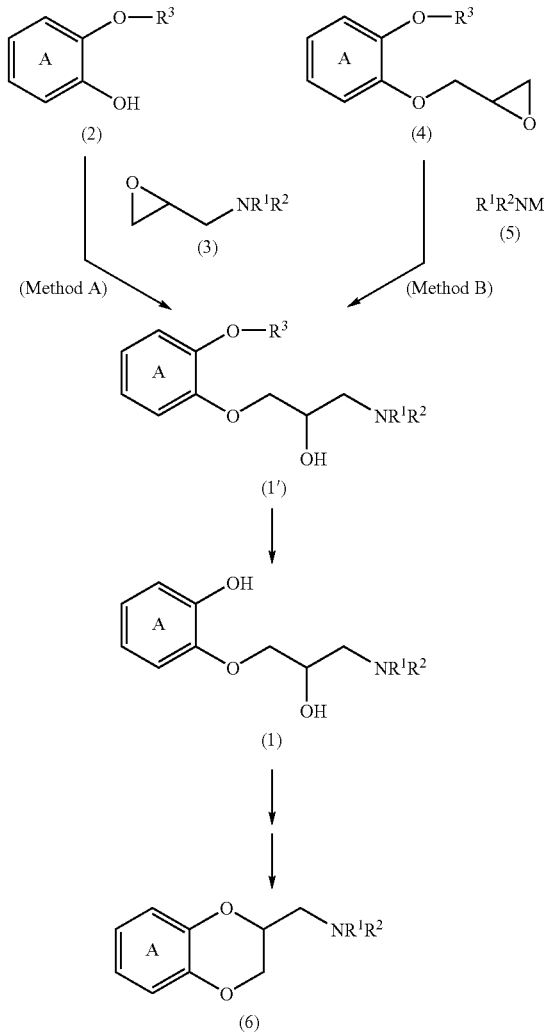

The definitions of signals of the above formulas are the same as defined above.

According to the present invention, an 2-amidomethyl-1, 4-benzodioxane derivative (6) is prepared in highly chemical purity, and especially in regard to its optically active compound, it is prepared in highly optical purity without racemilization.

In regard to the definitions of the compounds related to the present invention, cycle A may further have 1 to 4 substituents, and the substituents at positions 3 and 6, or at positions 4 and 5 on the cycle A are different each other. These substituents are not limited as far as they do not give an effect to the reaction of the present invention. Examples of the substituent are saturated or unsaturated C1-4 alkyl group, such as methyl group, ethyl group, n-propyl group, isopropyl group, n-butyl group, sec-butyl group, tert-butyl group, allyl group, etc.; aralkyl group in which the alkyl moiety has 1 to 4 carbon atoms, such as benzyl group, phenethyl group, cinnamyl group, etc.; aryl group, such as phenyl group, tolyl group, etc.; halogen atom, such as fluorine atom, chlorine atom, bromine atom, iodine atom; halogenated C1-4 alkyl group, such as trifluoromethyl group, chloromethyl group, etc.; C2-5 alkanoyl group, such as acetyl group, propionyl group, pivaloyl group, etc.; mono or dialkylcarbamoyl group in which the alkyl moiety has 1 to 4 carbon atoms, such as N-methylcarbamoyl group, N,N-diethylcarbamoyl group, etc.; cyano group; nitro group and so on. Furthermore, other ring may be fused at both positions 3 and 4, or at both positions 5 and 6 on the cycle A to form a condensed polycyclic hydrocarbon with the cycle A, such as naphthalene, phenanthrene, 1,2,3,4-tetrahydronaphthlene, etc. Preferable cycle A is a benzene ring substituted by alkyl group or halogen atom, preferably by halogen atom.

In regard to the definitions of the compounds related to the present invention, $R^1$ means alkanoyl group such as C2-5 alkanoyl group, e.g., acetyl group, butyryl group, etc. or aroyl group such as benzoyl group, etc. and $R^2$ means hydrogen atom, alkanoyl group such as C2-5 alkanoyl group e.g., acetyl group, butyryl group, etc. or aroyl group such as benzoyl group, etc. Furthermore, $R^1$ and $R^2$ may be combined with the N atom to form cyclic imide group such as succinyl group, phthaloyl group, etc.

An 1-amido-3-(2-hydroxyphenoxy)-2-propanol derivative (1) of the present invention is prepared by condensing reacting an 2-alkoxyphenol (2) and glycidylamide (3), followed by elimination of the substituent $R^3$ (Method A), or by condensing an 2-alkoxyphenyl glycidyl ether (4) and an amide derivative (5), followed by elimination of the substituent $R^3$ (Method B).

$R^3$ in an 2-alkoxyphenol (2) which is a starting material of Method A means saturated or unsaturated C1-4 alkyl group or aralkyl group in which the alkyl group has 1 to 4 carbon atoms, such as methyl group, ethyl group, n-propyl group, isopropyl group, n-butyl group, sec-butyl group, tert-butyl group, allyl group, benzyl group, phenethyl group, cinnamyl group, etc., preferably methyl group, allyl group, benzyl group, and more preferably methyl group.

Examples of the glycidylamide (3) which is a starting material of Method A are N-glycidylacetoamide, N-glycidylhexaneamide, N-glycidylbenzamide, N-glycidyldibenzamide, N-glycidylsuccinimide, N-glycidylphthalimide, preferably N-glycidylphthalimide.

The amount of the glycidylamide (3) is preferably 0.5 to 2 molar equivalents to an 2-alkoxyphenol (2).

The N-glycidylamide (3) is prepared by for example, acylating the amine portion of 1-amino-3-chloro-2-propanol, followed by cyclization in a base (WO 99/024393). N-Glycidylphthalimide is prepared by reacting phthalimide and epihalohydrin (U.S. Pat. No. 5,608,110).

Fluoride salt used in condensing procedure in Method A includes alkali metal salt or alkaline earth metal salt. Examples of the alkali metal salt are lithium fluoride, sodium fluoride, potassium fluoride, cesium fluoride, etc. and examples of the alkaline earth metal are magnesium fluoride, potassium fluoride, etc. Fluoride salt supported in a suitable carrier such as celite, alumina, silica gel, molecular sieve, etc. may be used.

The alkali metal carbonate used in condensing procedure in Method A includes lithium carbonate, sodium carbonate, potassium carbonate, cesium carbonate, etc. and the alkali metal hydrogencarbonate includes lithium hydrogencarbonate, sodium hydrogencarbonate, potassium hydrogencarbonate, cesium hydrogencarbonate, etc.

The above fluoride salt, alkali metal carbonate and alkali metal hydrogencarbonate may be used solely or in a combination thereof. The amount is used in stoichiometric amount or catalystic amount, preferably 0.01 to 3 molar equivalents to an 2-alkoxyphenol (2).

The solvent used in condensing procedure in Method A includes an aprotic polar solvent such as N,N-dimethylformamide (DMF), dimethyl sulfoxide (DMSO), hexamethylphosphorylamide, acetonitrile, etc.; an ester-solvent such as ethyl acetate, butyl acetate, etc.; an ether-solvent such as diethyl ether, tert-butyl methyl ether, 1,2-dimethoxyethane, 1,4-dioxane, tetrahydrofuran (THF), etc.; a ketone-solvent such as acetone, 2-butanone, methyl isobutyl ketone, etc., preferably DMF, acetonitrile, and THF, and more preferably DMF. These solvents may be used solely or in a combination of them. The ratio of the mixture is not limited. The amount of the solvent is preferably used 2 to 20 times (w/w) to the amount of an 2-alkoxyphenol (2).

The condensing in Method A is carried out at preferably −10 to 180° C., more preferably 20 to 150° C. When the reaction is carried out below −10° C., it is not preferable as the reaction is suppressed. When the reaction temperature is beyond 180° C., the side reaction occurs and the yield decreases.

An 2-alkoxyphenyl glycidyl ether (4) used as a starting material in Method B is prepared by condensing an 2-alkoxyphenol (2) and epihalohydrin, for example in a base, in the two layer-system of nonaqueous solvent/aqueous solvent (WO 2004/002974) or by condensing an 2-alkoxyphenol (2) and glycidylsulfonate in the presence of fluoride salt (WO 98/12186).

The amide derivative (5) used in the condensing step of Method B includes acetoamide, hexaneamide (capronamide), benzamide, dibenzamide, succinimide, phthalimide, etc. An alkali metal salt thereof may be used. A preferable compound (5) is phthalimide. The amount of the amide derivative (5) is preferably 0.5 to 2 molar equivalents to the 2-alkoxyphenyl glycidyl ether (4).

The quaternary ammonium salt in condensing procedure in Method B means a salt consisting of an ammonium ion having substituents which may be different each other (such as saturated or unsaturated C1-16 alkyl group, aryl group, aralkyl group, etc.) and a pair ion (such as chloro ion, bromo ion, iodo ion, sulfuric acid ion, hydroxy ion, etc.). Examples of it are benzyl trimethylammonium chloride, diallyl dimethylammonium chloride, benzyl trimethylammonium bromide, n-octyl trimethylammonium bromide, stearyl trimethylammonium bromide, cetyl dimethylethylammonium bromide, tetra n-butylammonium iodide, β-methylcholine iodide, tetra-n-butylammonium hydrogensulfide, phenyl trimethylammonium hydroxide, etc.

Examples of the alkali metal carbonate and alkali metal hydrogencarbonate used in the condensing step of Method B are the same as the compounds used in the above method A.

The above quaternary ammonium salt, alkali metal carbonate and alkali metal hydrogencarbonate may be used solely or in a mixture thereof. The amount of it is used in stoichiometric amount or catalystic amount, preferably 0.01 to 3 molar equivalents to an 2-alkoxyphenyl glycidyl ether (4).

The solvent used in condensing procedure in Method B includes an alcohol such as methanol, ethanol, 1-propanol, isopropanol, 1-butanol, 2-butanol, tert-butanol, cyclohexanol, etc., an ether-solvent such as diethyl ether, dibutyl ether, tert-butyl methyl ether, 1,2-dimethoxyethane, 1,4-dioxane, THF. etc., an aprotic polar solvent such as DMF, DMSO, hexamethylphosphorylamide, acetonitrile, etc., preferably methanol, isopropanol, tert-butanol, THF, DMF and acetonitrile. These solvents are used solely or in a mixture thereof. The ratio of the mixture is not limited. The amount of the solvent is preferably used 2 to 20 times (w/w) to the amount of an 2-alkoxyphenyl glycidyl ether (4).

The reaction temperature in the condensing step of Method B is preferably −10 to 180° C., more preferably 20 to 150° C. When the reaction is carried out below −10° C., it is not preferable as the reaction is suppressed. When the reaction temperature is beyond 180° C., the side reaction occurs and the yield decreases.

Substituent $R^3$ in an 3-(2-alkoxyphenoxy)-1-amido-2-propanol derivatives (1'), a condensed compound prepared by method A or method B can be eliminated for example, by using a silyl reagent, such as trimethylsilyl iodide, trimethylsilyl chloride-sodium iodide, trimethylsilyl chloride-sodium sulfide; an acidic reagent such as boron tribromide, aluminum chloride; or a basic reagent such as potassium tert-butoxide-18 crown 6, sodium thioethoxide, sodium N-methylaniline. When the substituent $R^3$ is allyl group or benzyl group, the substituent can be eliminated by hydrogenesis under Pd/C.

Thus obtained 1-amido-3-(2-hydroxyphenoxy)-2-propanol derivative (1) is low in the solubility in an acetate such as methyl acetate, ethyl acetate, a halogen compound such as methylene chloride, chloroform, 1,2-dichloroethane, furthermore, a hydrocarbon-solvent such as toluene, benzene, n-hexane, n-heptane and water, and especially when $R^1$ and $R^2$ in the compound (1) form phthaloyl group with the N atom, the compound dissolves more hard in such solvents. Therefore, when the crude product (1) prepared is washed with these solvents, only the impure products dissolve in the solvent. Thus by filtrating an 1-amido-3-(2-hydroxyphenoxy)-2-propanol derivative (1) is easily obtainable in high purity.

In regard to thus obtained 1-amido-3-(2-hydroxyphenoxy)-2-propanol derivative (1), after the aromatic hydroxy group on the cycle A is selectively acylated, the secondary hydroxy group is converted to releasing group by sulfonylation and so on, and then thus obtained compound is subjected to intramolecular cyclization to easily obtain 2-amido-1,4-benzodioxane derivative (6).

The selective acylation of the aromatic hydroxy group on an 1-amido-3-(2-hydroxyphenoxy)-2-propanol derivative (1) is carried out by reacting the hydroxy group with an acid anhydride in a suitable solvent (a chloro compound such as 1,2-dichloroethne, etc., an ester-solvent such as ethyl acetate, etc., an ether-solvent such as diethyl ether, THF, etc.), in the presence of an alkali metal carbonate, an alkaline earth metal carbonate, or an alkali metal acetate, etc. The acid anhydride includes acetic anhydride, monochloro acetic anhydride, trifluoroacetic anhydride, etc. Examples of the alkali metal carbonate and alkali metal hydrogencarbonate are the same as mentioned above. The alkali metal acetate includes sodium acetate, potassium acetate, etc.

The conversion of the secondary alcohol of the acylated compound, namely 3-(2-acyloxyphenoxy)-1-amido-2-propanol to the leaving group, for example the sulfonylation is carried out in the presence of a suitable base (such as triethylamine, pyridine, etc.) with a corresponding sulfonyl chloride or sulfonic anhydride. The sulfonyl chloride and sufonic acid anhydride include methanesulfonyl chloride, trifluoromethanesulfonyl chloride, p-toluenesulfonyl chloride, or m-nitrobenzenesulfonyl chloride, methanesulfonic anhydride, trifluoromethanesulfonic anhydride, toluenesulfonic anhydride, etc.

Phosphynation may be carried out by using triphenylphosphine-diethyl azodicarboxylate (DEAD), etc. instead of the sulfonylation, The intramolecular cyclization reaction of the sulfonylated compound, namely 3-(2-acyloxyphenoxy)-1-amido-2-sulfonyloxypropane is carried out by adding a base in an alcohol-solvent such as methanol or ethanol. The base includes an alkali metal carbonate, an alkali metal hydrogencarbonate, an alkali metal alkoxide, etc. Examples of the alkali metal carbonate and alkali metal hydrogencarbonate are the same as mentioned above. Examples of the alkali metal alkoxide are sodium methoxide, potassium methoxide, sodium ethoxide, potassium ethoxide, sodium n-propoxide, sodium isopropoxide, potassium tert-butoxide, potassium tert-amylate, etc.

The intramolecular cyclization reaction is carried out preferably at −30 to 130° C., more preferably 0 to 100° C. When the reaction is carried out below −30° C., it is not preferable as the reaction is suppressed. When the reaction temperature is beyond 130° C., the side reaction occurs and the yield decreases.

An 2-amidomethyl-1,4-benzodioxane derivative (6) is prepared in high purity and good yield by the very simple method, namely by adding a solvent for extraction to the reaction mixture thus obtained after the cyclization reaction and washing, if necessary by subjecting to purification by column chromatography or recrystallization. The solvent for extract is not limited as far as it is a non aqueous solvent and can dissolve an 2-amidomethyl-1,4-benzodioxane derivative (6) such as an acetate e.g., methyl acetate, ethyl acetate, a hologenated compound, e.g., methylene chloride, chloroform, 1,2-dichloroethane, etc.

If an optically active 2-amidomethyl-1,4-benzodioxane derivative (6) is desired, it is obtainable by using an optically active isomer of the glycidylamide (3), the 2-alkoxyphenyl glycidyl ether (4) or the 1-amido-3-(2-hydroxyphenoxy)-2-propanol derivative (1) as a starting material. When these compounds are used in highly optical purity, the object compound, namely an 2-aminomethyl-1,4-benzodioxane derivative (6) can be obtained in keeping the original optical purity.

$R^1$ and $R^2$ of thus obtained 2-amidomethyl-1,4-benzodioxane derivative (6) are easily removed by the known method. The removing method consists in hydrolysis of it in hydrochloric acid solution under heating, by heating it in an aqueous acidic solution after heating in the presence of hydrazine hydrate in an alcoholic solvent, by treating it by an aqueous methylamine solution, by treating it with acetic acid after reacting with sodium borohydride, by reacting it with sodium sulfide in an aqueous THF solution and so on.

EXAMPLE

The present invention is explained in detail by the following examples, but the present invention should not be limited by these examples.

Example 1

(R)-1-(4-chloro-2-hydroxyphenoxy)-3-phthalimido-2-propanol (Method A)

To a reaction vessel were added phthalimide 4.00 g (27.2 mmol), (R)-epichlorohydrin 4.52 g (49.0 mmol), benzyl trimethylammonium chloride 126 mg (0.68 mmol) and isopropanol 25 mL, and the mixture was stirred at 40° C. for 24 hours. To this mixture were dropped a mixture of potassium tert-butoxide 3.66 g (32.6 mmol) and isopropanol 15 mL and the mixture was stirred at 20° C. for 3 hours. After evaporation of the solvent, the condensed residue was dissolved in ethyl acetate and washed with water. The organic layer was taken and recrystallized to give (R)-glycidylphthalimide 4.90 g (Yield 89%, chemical purity 96%) as a white crystal.

$^1$HNMR (CDCl$_3$, 270 MHz) δ2.70 (dd, 1H), 2.81 (dd, 1H), 3.21-3.28 (m, 1H), 3.81 (dd, 1H), 3.97 (dd, 1H), 7.27-7.91 (m, 4H) $^{13}$CNMR (CDCl$_3$, 68 MHz) δ39.8, 46.3, 49.2, 123.4, 131.9, 134.1, 167.9

To a reaction vessel were added (R)-glycidylphthalimide 4.06 g (20.0 mmol) obtained above, 4-chloro-2-methoxyphenol 3.17 g (20.0 mmol), cesium fluoride 0.608 g (4.0 mmol) and DMF 30 mL, and the mixture was stirred at 80° C. for 38 hours. After evaporation of the solvent, to the condensed residue was added 1,2-dichloroethane and the mixture was washed with an aqueous 3% NaOH solution, an aqueous 1% HCl solution and an aqueous 3% NaCl solution successively. The organic layer was taken and evaporated to give crude (R)-1-(4-chloro-2-methoxyphenoxy)-3-phthalimido-2-propanol 6.21 g (yield 87%, chemical purity 96%) as a pale yellow solid.

$^1$HNMR (CDCl$_3$, 270 MHz) δ3.17 (br, 1H), 3.80 (s, 3H), 3.88-4.11 (m, 4H), 4.23-4.32 (m, 1H), 6.83-6.86 (m, 3H), 7.71-7.88 (m, 4H) $^{13}$CNMR (CDCl$_3$, 68 MHz) δ40.9, 55.9, 68.5, 72.5, 112.4, 116.0, 120.3, 123.2, 126.9, 131.8, 133.9, 146.6, 150.3, 168.3

To a reaction vessel were added crude (R)-1-(4-chloro-2-methoxyphenoxy)-3-phthalimido-2-propanol 724 mg (2.00 mmol) obtained above, sodium iodide 899 mg (6.00 mmol) and 1,2-dichloroethane 5 mL. After adding chlorotrimethylsilane 435 mg (4.0 mmoL), the mixture was stirred at 60° C. for 35 hours (chemical purity after reaction: 62%). After cooled to room temperature, an aqueous 5% sodium thiosulfate solution was added and the solvent was removed. To the reaction residue was added toluene and the mixture was well suspended. The insoluble material was taken by filtration, washed with toluene and dried to give (R)-1-(4-chloro-2-hydroxyphenoxy)-3-phthalimido-2-propanol 521 mg (yield 75%, chemical purity 96%) as a pale yellow powder.

m.p. 214-218° C. Specific rotation $[\alpha]_D^{25}$ −28° (c0.05, CH$_3$CN) $^1$HNMR (DMSO-d$_6$, 270 MHz) δ3.66-3.81 (m, 2H), 3.88-4.00 (m, 2H), 4.12-4.19 (m, 1H), 5.31 (br, 1H), 6.75-6.93 (m, 3H), 7.82-7.90 (m, 4H), 9.32 (br, 1H) $^{13}$CNMR (DMSO-d$_6$, 68 MHz) δ41.0, 66.3, 71.5, 114.9, 115.3, 118.5, 122.8, 124.5, 131.6, 134.1, 145.6, 147.7, 167.8.

Example 2

(Method A)

To a reaction vessel were added (R)-glycidylphthalimide 5.80 g (28.6 mmol), 4-chloro-2-methoxyphenol 3.17 g (20.0 mmol), potassium carbonate 2.76 g (20 mmol) and DMF 60 mL, and the mixture was stirred at 80° C. for 46 hours. After evaporation of the solvent, to the condensed residue was added 1,2-dichloroethane and the mixture was washed with an aqueous 3% NaOH solution, an aqueous 1% HCl solution and an aqueous 5% NaCl solution successively. The organic layer was taken, and the solvent was evaporated to give (R)-1-(4-chloro-2-methoxyphenoxy)-3-phthalimido-2-propanol 4.20 g (yield 59%, chemical purity 90%) as a pale yellow solid.

Example 3

(Method B)

To a reaction vessel were added 4-chloro-2-methoxyphenol 20.0 g (126 mmol), (S)-epichlorohydrin 23.3 g (252 mmol), benzyl trimethylammonium chloride 0.585 g (3.15 mmol), toluene 40 mL and water 40 mL. To this mixture was dropped an aqueous 24% NaOH solution 31.5 g (189 mmol) in an ice bath, and the mixture was stirred at room temperature for 36 hours. The water layer was removed and the organic layer was washed with an aqueous 5% HCl solution and a 5% NaCl solution successively. The organic layer was taken and the solvent was evaporated to give crude (R)-glycidyl 4-chloro-2-methoxyphenyl ether 22.1 g (yield 87%, chemical purity 93%) as a white solid.

$^1$HNMR (CDCl$_3$, 270 MHz) δ2.73 (dd, 1H), 2.90 (dd, 1H), 3.34-3.40 (m, 1H), 3.86 (s, 3H), 3.98 (dd, 1H), 4.24 (dd, 1H), 6.82-6.89 (m, 3H) $^{13}$CNMR (CDCl$_3$, 68 MHz) δ44.6, 50.0, 56.0, 70.4, 112.3, 114.8, 120.1, 126.4, 146.5, 150.0

To a reaction vessel were added phthalimido 442 mg (3.00 mmol), crude (R)-glycidyl-4-chloro-2-methoxyphenyl ether 664 mg (3.00 mmol), benzyl trimethylammonium chloride 55.7 mg (0.30 mmol) and acetonitrile 6 mL and the mixture was stirred at 70° C. for 24 hours. After evaporation of the solvent, to the condensed residue was added 1,2-dichloroethane and the mixture was washed with water. The organic layer was taken and the solvent was evaporated to give crude (R)-1-(4-chloro-2-methoxyphenoxy)-3-phthalimido-2-propanol 1.14 g (yield 102%, chemical purity 86%) as a pale yellow solid.

Crude (R)-1-(4-chloro-2-methoxyphenoxy)-3-phthalimido-2-propanol was treated in the same manner as the above example 1 (Method A) to give (R)-1-(4-chloro-2-hydroxyphenoxy)-3-phthalimido-2-propanol as a pale yellow powder.

Example 4

(S)-1-(4-chloro-2-hydroxyphenoxy)-3-phthalimido-2-propanol (Method B)

4-Chloro-2-methoxyphenol 60.0 g (378 mmol) and (R)-epichlorohydrin 70.0 g (757 mmol) were treated in the same manner as example 3 to give (S)-1-(4-chloro-2-hydroxyphenoxy)-3-phthalimido-2-propanol 79.3 g (yield 60%, chemical purity 98%) as a pale yellow powder.

Specific rotation $[\alpha]_D^{25}$ +31° (c0.05, CH$_3$CN)

Example 5

(S)-7-Chloro-2-(phthalimidomethyl)-1,4-benzodioxane

To a reaction vessel were added (R)-1-(4-chloro-2-hydroxyphenoxy)-3-phthalimido-2-propanol 348 mg (1.00 mmol), sodium carbonate 159 mg (1.50 mmol) and 1,2-dichloroethane 4 mL. After to the mixture was dropped acetic anhydride 122 mg (1.20 mmol), the mixture was stirred at room temperature for 15 hours. After terminating the reaction by adding water, the water layer was removed and the organic layer was washed with an aqueous 5% HCl solution and an aqueous 5% NaCl solution successively. The organic layer was taken and the solvent was evaporated to give crude (R)-1-(4-chloro-2-acetoxyphenoxy)-3-phthalimido-2-propanol 372 mg (yield 92%, chemical purity 97%) as a pale yellow solid.

$^1$HNMR (CDCl$_3$, 270 MHz) δ2.41 (s, 3H), 2.83 (br, 1H), 3.86-3.98 (m, 2H), 4.04-4.14 (m, 2H), 4.19-4.29 (m, 1H), 6.89-7.19 (m, 3H), 7.70-7.90 (m, 4H) $^{13}$CNMR (CDCl$_3$, 68 MHz) δ20.7, 40.9, 68.4, 76.5, 114.1, 123.1, 123.3, 125.9, 126.6, 131.8, 134.0, 140.1, 148.5, 168.5, 168.9

To a reaction vessel were added crude (R)-1-(4-chloro-2-acetoxyphenoxy)-3-phthalimido-2-propanol 364 mg (0.90 mmol), triethylamine 137 mg (1.36 mmol) and ethyl acetate 2 mL. To this mixture was slowly dropped methanesulfonyl chloride 134 mg (1.18 mmol) in an ice bath and then the mixture was stirred at room temperature for 3 hours. After washing with an aqueous 5% HCl solution and water successively, the organic layer was taken and the solvent was evaporated to give crude (R)-1-(4-chloro-2-acetoxyphenoxy)-2-methanesulfonyloxy-3-phthalimidopropane 213 mg (yield 98%, chemical purity 97%) as a brown solid.

$^1$HNMR (CDCl$_3$, 270 MHz) δ2.39 (s, 3H), 3.09 (s, 3H), 3.95 (dd, 1H), 4.18 (dd, 1H), 4.21 (dd, 2H), 5.25-5.33 (m, 1H), 6.87-7.21 (m, 3H), 7.73-7.90 (m, 4H) $^{13}$CNMR (CDCl$_3$, 68 MHz) δ20.6, 38.4, 38.5, 68.4, 75.4, 114.2, 123.4, 123.5, 126.4, 126.6, 131.6, 134.1, 140.2, 148.2, 167.8, 168.6

To a reaction vessel were added crude (R)-1-(4-chloro-2-acetoxyphenoxy)-2-methanesulfonyloxy-3-phthalimidopropane 242 mg (0.50 mmol), sodium carbonate 58.3 mg (0.60 mmol) and methanol 2 mL, and the mixture was stirred at 50° C. for 9 hours. To the reaction mixture was added ethyl acetate and the mixture was washed with water. The solvent was evaporated and recrystallized to give (S)-7-chloro-2-(phthalimidomethyl)-1,4-benzodioxane 114 mg (yield 70%, chemical purity 98%, optical purity 98% ee) as a white solid.

m.p. 174-176° C. Specific rotation $[\alpha]_D^{25}$ −75° (c0.5, CH$_3$CN) $^1$HNMR (DMSO-d$_6$, 270 MHz) δ3.88 (dd, 2H), 4.14 (dd, 1H), 4.33 (dd, 1H), 4.48-4.54 (m, 1H), 6.84-6.93 (m, 3H), 7.84-7.93 (m, 4H) $^{13}$CNMR (DMSO-d$_6$, 68 MHz) δ37.3, 64.9, 70.3, 116.7, 117.9, 120.8, 122.9, 124.4, 131.2, 134.2, 141.5, 142.7, 167.3

The optical purity (% ee) was calculated using HPLC and by its area ratio under following conditions.

Column: CHIRALPAC AD-RH (0.46 cmφ×15 cmL) by Daicel Chemical Ind.
Mobile phase: acetonitrile/water (50/50 (v/v))
Velocity: 1.2 mL/min.
Detection: UV 220 nm
Retention: (R) isomer=about 19.7 min., (S) isomer=21.8 min.

Example 6

(R)-7-Chloro-2-(phthalimidomethyl)-1,4-benzodioxane (S)-1-(4-Chloro-2-hydroxyphenoxy)-3-phthalimido-2-propanol 67.0 g (193 mmol) was treated in the same manner as example 5 to give (R)-7-chloro-2-(phthalimidomethyl)-1,4-benzodioxane 44.8 g (yield 71%, chemical purity 99%, optical purity 99% ee) as a white solid. Specific rotation $[\alpha]^{D25}$ +78° (c0.5, CH$_3$CN).

What is claimed is:

1. An 1-amido-3-(2-hydroxyphenoxy)-2-propanol derivative represented by the following formula (1),

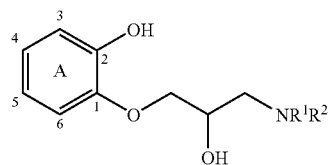

wherein cycle A may further have 1 to 4 substituents, and said substituent means a substituent selected from the group consisting of saturated or unsaturated C1-4 alkyl group, aralkyl group in which the alkyl moiety has 1 to 4 carbon atoms, aryl group, halogen atom, halogenated C1-4 alkyl group, C2-5 alkanoyl group, mono or dialkylcarbamoyl group in which the alkyl moiety has 1 to 4 carbon atoms, cyano group and nitro group, and the substituents at positions 3 and 6, or at positions 4 and 5 on the cycle A are different from each other, another ring may be fused at positions 3 and 4, or at positions 5 and 6 on the cycle A to form a condensed polycyclic hydrocarbon with the cycle A, R$^1$ is alkanoyl group or aroyl group, and R$^2$ is hydrogen atom, alkanoyl group or aroyl group, or R$^1$ and R$^2$ may be combined together with the N atom to form a cyclic imido group.

2. A process for preparing an 1-amido-3-(2-hydroxyphenoxy)-2-propanol derivative represented by the following formula (1),

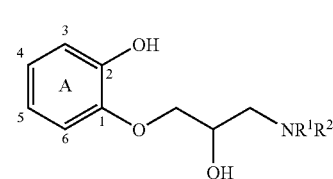

wherein cycle A, R$^1$ and R$^2$ are the same as defined above, which comprises reacting an 2-alkoxyphenol represented by the following formula (2),

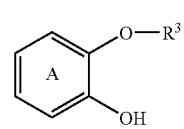

wherein cycle A is the same as defined above, R$^3$ is saturated or unsaturated C1-4 alkyl group, or aralkyl group in which the alkyl moiety has 1 to 4 carbon atoms, with a glycidylamide represented by the following formula (3),

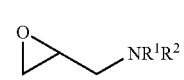

wherein R$^1$ and R$^2$ are the same as defined above, in the presence of fluoride salt, alkali metal carbonate or alkali metal hydrogencarbonate, and then eliminating a substituent R$^3$ to prepare the compound (1).

3. A process for preparing an 1-amido-3-(2-hydroxyphenoxy)-2-propanol derivative represented by the following formula (1),

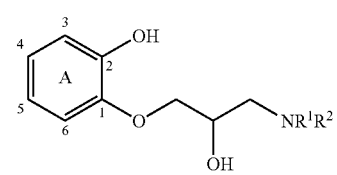

wherein cycle A, R$^1$ and R$^2$ are the same as defined above, which comprises reacting an 2-alkoxyphenyl glycidyl ether represented by the following formula,

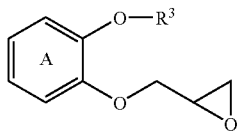

wherein cycle A and R³ are the same as defined above, and an amide derivative represented by the following formula (5),

wherein M is hydrogen atom or alkali metal and R¹ and R² are the same as defined above, in the presence of alkali metal carbonate, alkali metal hydrogencarbonate or quaternary ammonium salt, and then eliminating the substituent R³ to give the compound (1).

4. A process for preparing an 2-amidomethyl-1,4-benzodioxane derivative represented by the following formula,

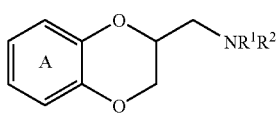

wherein cycle A, R¹ and R² are the same as defined above, which comprises converting the aromatic hydroxy group and the secondary hydroxy group of an 1-amido-3-(2-hydroxyphenoxy)-2-propanol derivative represented by the following formula (1),

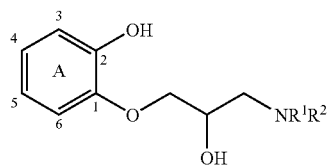

wherein cycle A, R¹ and R² are the same as defined above, to acyloxy group and leaving group, respectively, and then subjecting it to intramolecular cyclization reaction to prepare the compound (6).

5. The process for preparing an 2-amidomethyl-1,4-benzodioxane derivative according to claim 4 which comprises selectively acylating the aromatic hydroxy group of an 1-amido-3-(2-hydroxyphenoxy)-2-propanol derivatives (1) of the following formula,

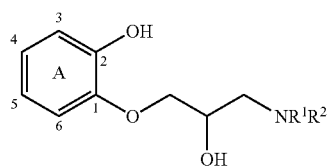

wherein cycle A, R¹ and R² are the same as defined above.

6. The process for preparing an 2-amidomethyl-1,4-benzodioxane derivative (6) according to claim 4 wherein the leaving group is sulfonyloxy group.

7. The process for preparing an 2-amidomethyl-1,4-benzodioxane derivative (6) according to claim 4 wherein the intramolecular cyclization reaction is carried out in a presence of a base in an alcohol-solvent.

8. The process for preparing an optically active 1-amido-3-(2-hydroxyphenoxy)-2-propanol derivative (1) or an optically active 2-amidomethyl-1,4-benzodioxane derivatives (6) according to claim 2 wherein a glycidylamide (3) or an 2-alkoxyphenyl glycidyl ether (4) is an optically active isomer.

9. The process for preparing of an 1-amido-3-(2-hydroxyphenoxy)-2-propanol derivative (1) or its optical isomer, or 2-amidomethyl-1,4-benzodioxane derivative (6) or its optical isomer according to claim 2 wherein the glycidylamide (3) is glycidylphthalimide.

10. The process for preparing of an 1-amido-3-(2-hydroxyphenoxy)-2-propanol derivative (1) or its optical isomer, or an 2-amidomethyl-1,4-benzodioxane derivative (6) or its optical isomer according to claim 3 wherein the amide derivative (5) is phthalimide.

11. The process for preparing of an 1-amido-3-(2-hydroxyphenoxy)-2-propanol derivative (1) or its optical isomer, or an 2-amidomethyl-1,4-benzodioxane derivative (6) or its optical isomer according to claim 2 wherein the substituent on the cycle A is halogen atom.

12. The process for preparing of an 1-amido-3-(2-hydroxyphenoxy)-2-propanol derivative (1) or its optical isomer, according to claim 2 wherein R³ of the 2-alkoxyphenol (2) or 2-alkoxyphenyl glycidyl ether (4) is methyl group.

13. A process for preparing an 2-amidomethyl-1,4-benzodioxane derivative represented by the following formula,

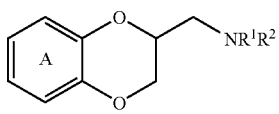

wherein cycle A, R¹ and R² are the same as defined above, which comprises reacting an 2-alkoxyphenol represented by the following formula (2),

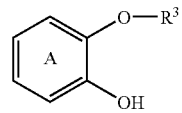

wherein cycle A and R³ are the same as defined above, and a glycidylamide represented by the following formula (3),

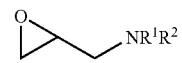

wherein R¹ and R² are the same as defined above, in the presence of fluoride salt, alkali metal carbonate or alkali metal hydrogencarbonate, and then eliminating the substituent R³ to prepare an 1-amido-3-(2-hydroxyphenoxy)-2-propanol derivative represented by the following formula (1),

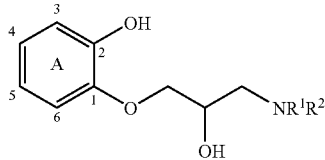

wherein cycle A, $R^1$ and $R^2$ are the same as defined above, or reacting an 2-alkoxyphenyl glycidyl ether represented by the following formula (4),

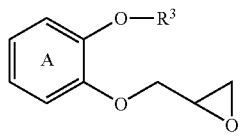

wherein cycle A and $R^3$ are the same as defined above, and an amide derivative represented by the following formula (5), $$R^1R^2NM \qquad (5)$$

wherein M, $R^1$ and $R^2$ are the same as defined above, in the presence of alkali metal carbonate, alkali metal hydrogencarbonate or quaternary ammonium salt, and then eliminating the substituent $R^3$ to prepare the compound (1), and then, converting the aromatic hydroxy group and the secondary hydroxy group of the compound (1) to acyloxy group and leaving group, respectively and then subjecting it to intramolecular cyclization reaction to prepare the compound (6).

14. The process for preparing an optically active 1-amido-3-(2-hydroxyphenoxy)-2-propanol derivative (1) or an optically active 2-amidomethyl-1,4-benzodioxane derivatives (6) according to claim 3 wherein a glycidylamide (3) or an 2-alkoxyphenyl glycidyl ether (4) is an optically active isomer.

15. The process for preparing an optically active 1-amido-3-(2-hydroxyphenoxy)-2-propanol derivative (1) or an optically active 2-amidomethyl-1,4-benzodioxane derivatives (6) according to claim 4 wherein a glycidylamide (3) or an 2-alkoxyphenyl glycidyl ether (4) is an optically active isomer.

16. The process for preparing of an 1-amido-3-(2-hydroxyphenoxy)-2-propanol derivative (1) or its optical isomer, or 2-amidomethyl-1,4-benzodioxane derivative (6) or its optical isomer according to claim 4 wherein the glycidylamide (3) is glycidylphthalimide.

17. The process for preparing of an 1-amido-3-(2-hydroxyphenoxy)-2-propanol derivative (1) or its optical isomer, or an 2-amidomethyl-1,4-benzodioxane derivative (6) or its optical isomer according to claim 4 wherein the amide derivative (5) is phthalimide.

18. The process for preparing of an 1-amido-3-(2-hydroxyphenoxy)-2-propanol derivative (1) or its optical isomer, or an 2-amidomethyl-1,4-benzodioxane derivative (6) or its optical isomer according to claim 3 wherein the substituent on the cycle A is halogen atom.

19. The process for preparing of an 1-amido-3-(2-hydroxyphenoxy)-2-propanol derivative (1) or its optical isomer, or an 2-amidomethyl-1,4-benzodioxane derivative (6) or its optical isomer according to claim 4 wherein the substituent on the cycle A is halogen atom.

20. The process for preparing of an 1-amido-3-(2-hydroxyphenoxy)-2-propanol derivative (1) or its optical isomer, according to claim 3 wherein $R^3$ of the 2-alkoxyphenol (2) or 2-alkoxyphenyl glycidyl ether (4) is methyl group.

21. An 1-amido-3-(2-hydroxyphenoxy)-2-propanol derivative represented by the following formula (1),

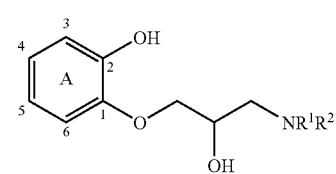

wherein cycle A may further have 1 to 4 substituents, and said substituent means a substituent selected from the group consisting of saturated or unsaturated C1-4 alkyl group; benzyl, phenethyl, cinnamyl, phenyl, tolyl, halogen atom, halogenated C1-4 alkyl group, C2-5 alkanoyl group, mono or dialkylcarbamoyl group in which the alkyl moiety has 1 to 4 carbon atoms, cyano group and nitro group, and the substituents at positions 3 and 6, or at positions 4 and 5 on the cycle A are different from each other, another ring may be fused at positions 3 and 4, or at positions 5 and 6 on the cycle A to form naphthalene, phenanthrene or 1,2,3,4-tetrahydronaphthalene, $R^1$ is C2-5 alkanoyl group or benzoyl, and $R^2$ is hydrogen atom, C2-5 alkanoyl group or benzoyl, or $R^1$ and $R^2$ may be combined together with the N atom to form succinyl or phthaloyl.

* * * * *